Aug. 5, 1969 D. L. ARMSTRONG Plant Pat. 2,915
ROSE PLANT
Filed Dec. 19, 1967
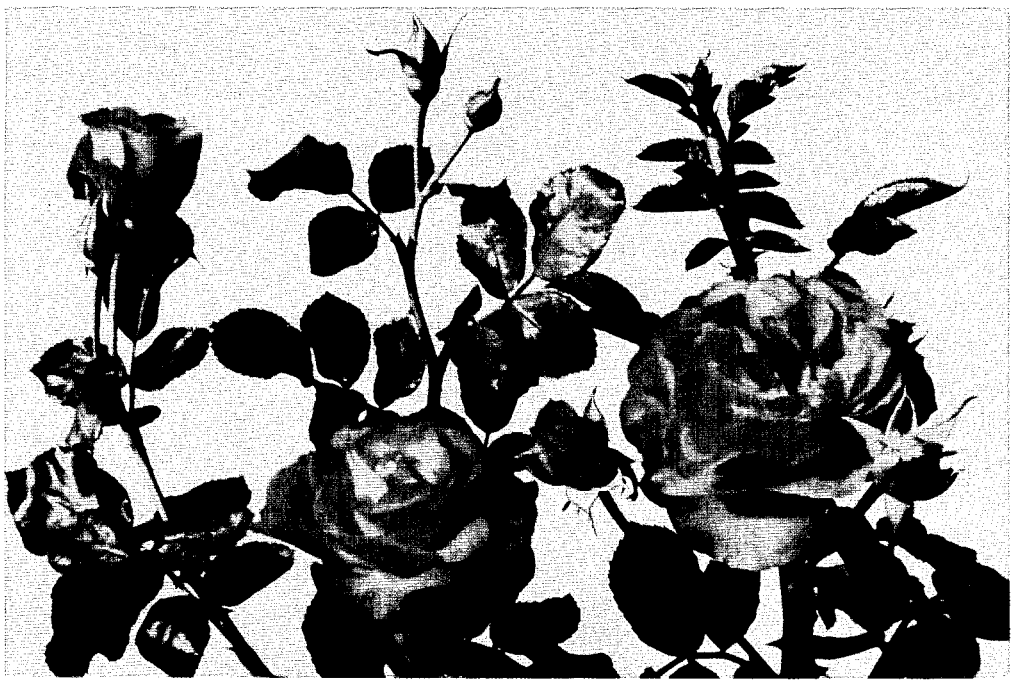
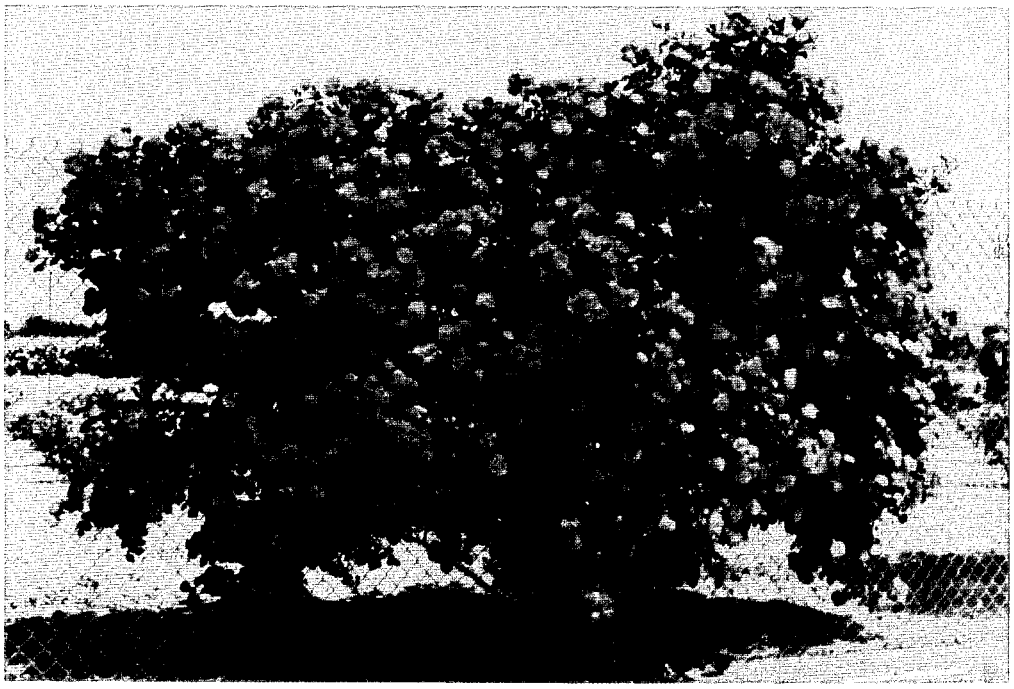
Inventor.
D. L. Armstrong
By: Robb & Robb
Attorneys.

United States Patent Office

Plant Pat. 2,915

Patented Aug. 5, 1969

2,915

ROSE PLANT

David L. Armstrong, Ontario, Calif., assignor to Armstrong Nurseries, Inc., Ontario, Calif., a corporation of California Filed Dec. 19, 1967, Ser. No. 691,917

Int. Cl. A01h 5/02

U.S. Cl. Plt.—6 1 Claim

The present invention relates to a new and distinct variety of rose plant of the pillar-climbing floribunda class, which was originated by me by crossing the rose variety known as "New Dawn" (Plant Patent No. 1) with an unnamed and unpatented climbing sport of the bush form of the rose variety known as "Embers" (Plant Patent No. 1,178), the variety "New Dawn" being the seed parent and the unnamed climbing sport being the pollent parent.

The new variety resulted from an extensive breeding program conducted by me and having for its objective to produce improved, everblooming, red-flowered, pillar-climber rose varieties, and it is one which fully achieves this objective, as evidenced by the following unique combination of characteristics which are outstanding therein and which distinguish the new variety from its parents, as well as from all other varieties of which I am aware:

(1) An everblooming, bushy, free-standing, vigorous, upright-spreading, climbing habit which can be left as a large, bushy shrub, or trained as a typical climbing plant having short to long arching or climbing canes up to five or six feet in length on established plants;

(2) Glossy foliage of medium to large size which covers the plant well and is quite disease resistant and attractive, resembling the foliage of the parent variety "New Dawn," though somewhat larger;

(3) A very floriferous habit similar to the bush form of the parent variety "Embers," with all canes terminating in small to medium size flower clusters and usually producing much lateral growth varying from simple, short flower clusters to new long canes also having flowers later in the same season, as well as some flowering from long canes the next season, said flowers of the clusters being double in form and highly attractive, progressing from a high-centered form to a more flat-cupped form in the fully open flower stage;

(4) Excellent flower substance and long-lasting qualities; and (5) A distinctive, attractive and relatively unfading flower color ranging between Cherry and Rose Red.

In comparison with its seed parent "New Dawn," the variety is primarily more floriferous, with the flowers borne in small to medium size clusters and being of red color instead of being borne in small clusters or singly and having a blush pink color like those of "New Dawn."

As compared with its unnamed climbing sport parent variety, the new variety has a more bushy and more branched plant habit and is everblooming, instead of having very long arching canes with a once-a-year blooming habit like this parent variety.

Asexual reproduction of my new variety by budding, as performed at Ontario, Calif., shows that the foregoing characteristics and distinctions come true to form and are established and transmitted through succeeding propagations.

The accompanying drawing shows a typical specimen plant of my new variety particularly illustrating its climbing and blooming habits, and also shows typical specimens of the flowers, stems and foliage on an enlarged scale, all as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Tall; pillar; climbing; outdoor; seedling, for cut flowers and for garden decoration.

Class: Floribunda climber.

Breeding: Seedling.

*Seed parent.*—"New Dawn."

*Pollen parent.*—An unnamed climbing sport of "Embers."

Propagation: Holds its distinguishing characteristics through succeeding propagations by budding.

FLOWER

Locality where grown and observed: Ontario, Calif.

Flowers borne: Sometimes two or three, but often five to ten or more to stem; in irregular clusters; on strong stems of short to medium length.

Quantity of bloom: Abundant, outdoors.

Continuity: Nearly continuous during growing season.

Fragrance: From slight to moderate.

Bud:

*Peduncle.*—From short to average length; average caliper; erect; smooth; with several to many small stipitate glands. Color—near Absinthe Green, Plate XXXI (R), overlaid with near Ochre Red, Plate XXVII (R) on side exposed to the sun.

*Before calyx breaks.*—Size—small. Form—short; broadly ovoid.

*As calyx breaks.*—Color—between China Rose, Plate 024, page 111 (W) and Spiraea Red, Plate 025/1, page 112 (W).

*Sepals.*—Sometimes with foliaceous appendages extending ¼ to ⅓ of sepal length. Inner surface—with fine, woolly tomentum. Outer surface—usually with several to many small stipitate glands. Alternate margins—lined with fine, wooly tomentum. Other margins—with several to many small stipitate glands and short, slender foliaceous parts.

*As first petal opens.*—Size—small. Form—short; broadly ovoid. Color: outside—between Cherry, Plate 722/1, page 157 (W) and Rose Red, Plate 724/1, page 158 (W), with small area at base of petal near Mimosa Yellow, Plate 602/2, page 143 (W); inside—between Currant Red, Plate 821/2, page 167 (W)) and Cardinal Red, Plate 822/2, page 168 (W), with small area at base of petal near Mimosa Yellow, Plate 602/2, page 143 (W).

*Opening.*—Opens up well; is not retarded or prevented from opening by cold, hot, wet or dry weather.

Bloom:

*Size (when fully open).*—From small to medium size; from 2¾ inches to 3¼ inches.

*Petalage.*—Double; from 25 to 30 petals, plus 2 to 5 petaloids; arranged irregularly.

*Form.*—Cupped and high-centered at first, but becoming flat to cupped; petals being at first tightly flat to cupped, but later becoming more loosely flat to cupped at maturity, with petals of both newly open and 3-days open flowers usually irregularly wavy, making them somewhat rigid; inner petals of both newly open and 3-days open flowers usually reflexed slightly inward.

Petals:

*Texture.*—Thick; leathery.

*Appearance.*—Inside—from satiny to velvety. Outside—satiny.

*Shape.*—Outside—between round and broadly obovate, with apex flat and sometimes with 1 or 2 notches. Intermediate—between round and broadly obovate, with apex rounded to flat and sometimes with 1 or 2 notches. Inside—between round and broadly obovate, with apex rounded.

This description of a newly opened flower was made from a rose grown outdoors during the month of October at Ontario, Calif.

*Color.*—Outer petal: outside surface—near Rose Red, Plate 724, page 158 (W), with small area at base of petal near Mimosa yellow, Plate 602/3, page 143 (W); inside surface—near Rose Red, Plate 724, page 158 (W), blending with near Rose Madder, Plate 23/1, page 23 (W) toward base of petal, and with small area at base of petal near Mimosa Yellow, Plate 602/3, page 143 (W). Intermediate petal: outside surface—between Cherry, Plate 722/2, page 157 (W) and Rose Red, Plate 724/2, page 158 (W), with small area at base of petal near Mimosa Yellow, Plate 602/3, page 143 (W); inside surface—near Cherry, Plate 722/1, page 157 (W), blending with near Crimson, Plate 22/1, page 22 (W) toward base of petal, with small area at base of petal near Mimosa Yellow, Plate 602/3, page 143 (W). Inner petal: outside surface—near Crimson, Plate 22, page 22 (W), with small area at base of petal near Mimosa Yellow, Plate 602/3, page 143 (W); inside surface—near Cherry, Plate 722/2, page 157 (W), blending with near Crimson, Plate 22/2, page 22 (W) toward base of petal, and with small area at base of petal near Mimosa Yellow, Plate 602/3, page 143 (W).

This description was made from a rose that was open for three days outdoors during the month of October at Ontario, Calif.:

*Color.*—Outer petal: outside surface—between Cherry, Plate 722/2, page 157 (W) and Rose Red, Plate 724/2, page 158 (W), with small area at base of petal near Mimosa Yellow, Plate 602/3, page 143 (W); inside surface—between Cherry, Plate 722, page 157 (W) and Rose Red, Plate 724/1, page 158 (W), with small area at base of petal near Mimosa Yellow, Plate 602/3, page 143 (W). Inner petal: outside surface—between Cherry, Plate 722/2, page 157 (W) and Rose Red, Plate 724/2, page 158 (W), with small area at base of petal near Mimosa Yellow, Plate 602/3, page 143 (W); inside surface—between Cherry, Plate 722, page 157 (W) and Rose Red, Plate 724/1, page 158 (W), with small area at base of petal near Mimosa Yellow, Plate 602/3, page 143 (W).

*General color effect.*—Newly opened flower—between Cherry, Plate 722/1, page 157 (W) and Rose Red, Plate 724/1, page 158 (W). Three days open—between Cherry, Plate 722, page 157 (W) and Rose Red, Plate 724, page 158 (W).

*Behavior.*—Drop off cleanly; not particularly affected by cold, hot, wet or dry weather.

*Flower longevity.*—On bush in garden—4 or 5 days in October. Cut roses grown outdoors and kept at living-room temperatures—3 or 4 days in October.

REPRODUCTIVE ORGANS

Stamens: From average number to many; arranged regularly about pistils; a few mixed with petaloids.

Filaments: From short to medium length (from 4 mm. to 8 mm. long); most with anthers. Color—near Empire Yellow, Plate 603/1, page 66 (W).

Anthers: Small; all open approximately at once. Color: upper side—margins near Maize Yellow, Plate 607/1, page 69 (W), with remainder near Empire Yellow, Plate 603/1, page 66 (W); under side—margins near Maize Yellow, Plate 607/1, page 69 (W), with remainder near Empire Yellow, Plate 603/1, page 66 (W).

Pollen: Moderate abundance. Color—near Cadmium Orange, Plate 8/1, page 8 (W).

Pistils: From few to average number (approximately 40 in number).

Styles: Uneven; from short to average length; thin; bunched. Color—upper ½ of style near Carmine Rose, Plate 621/1, page 75 (W), with remainder near Primrose Yellow, Plate 601/1, page 65 (W).

Stigma: Color—near Straw Yellow, Plate 604/1, page 67 (W).

Ovaries: Usually all enclosed in calyx.

Hips: Average length; globular; smooth; walls thick and fleshy. Color (mature)—near Zinc Orange, Plate XV (R).

Sepals: Falling soon; from medium length to long; straight. Color: inside—near Buffy Olive, Plate XXX (R); outside—near Olive-Yellow, Plate XXX (R).

Seeds: Few (from 10 to 20 in number); from medium size to large.

PLANT

Foliage:

*Leaves.*—Compound of usually 3–7 leaflets; abundant; from medium size to large; leathery; glossy.

*Leaflets.*—Shape—broadly oval. Apex—acute. Base—round. Margin—simply serrate.

*Color.*—Mature: upper surface—near Cress Green, Plate XXXI (R); under surface—near Biscay Green, Plate XVII (R). Young: upper surface—near Deep Dull Yellow-Green (1), Plate XXXII (R); under surface—near Courge Green, Plate XVII (R).

*Rachis (the supporting stem of the compound leaf.*—From average size to heavy. Upper side—grooved; with several to many small stipitate glands on edges. Under side—smooth; with none to few small prickles.

*Stipules.*—From short to medium length; medium width; with short points turning out at an angle of more than 45°.

*Disease resistance.*—Better than average resistance to mildew and blackspot, as determined by comparison with other varieties grown under comparable conditions at Ontario, Calif.

Growth:

*Habit.*—Bushy; upright-spreading; climbing; much-branched.

*Growth.*—Vigorous.

*Canes.*—Heavy.

*Main stems.*—Color—near Rainette Green, Plate XXXI (R). Large prickles—from several to many; medium length; hooked slightly downward; with medium length, broad base; color—near Sayal Brown, Plate XXIX (R). Small prickles—from none to few; color—near Sayal Brown, Plate XXIX (R). Hairs—none.

*Branches.*—Color—near Deep Chrysolite Green, Plate XXXI (R). Large prickles—from several to many; from short to medium length; hooked slightly downward; with short to medium length, broad base; color—near Cinnamon, Plate XXIX (R). Small prickles—from none to few; color—near Cinnamon, Plate XXIX (R). Hairs—none.

*New shoots.*—Color—near Apple Green, Plate XVII (R), overlaid with near Deep Chrysolite Green, Plate XXXI (R) on side exposed to the sun. Large prickles—from several to many; from short to medium length; hooked slightly downward; with short to medium length, narrow base; color—near Fawn Color, Plate XL (R). Small prickles—from none to few; color—near Fawn Color, Plate XL (R). Hairs—none.

I claim:

1. A new and distinct variety of rose plant of the pillar-climbing floribunda class, substantially as herein shown and described, characterized particularly as to novelty by the unique combination of an everblooming, bushy, free-standing, vigorous, upright-spreading, climbing habit which can be left as a large, bushy shrub, or trained as a typical climbing plant having short to long arching or climbing canes up to five or six feet in length on established plants, glossy foliage of medium to large size which covers the plant well and is quite disease resistant and attractive, resembling the foliage of the parent variety "New Dawn," though somewhat larger, a very floriferous habit similar to the bush form of the parent variety "Embers," with all canes terminating in small to medium size flower clusters and usually producing much lateral growth varying from simple, short flower clusters to new long canes also having flowers later in the same season, as well as some flowering from long canes the next season, said flowers of the clusters being double in form and highly attractive, progressing from a high-centered form to a more flat-cupped form in the fully open flower stage, excellent flower substance and long-lasting qualities and a distinctive, attractive and relatively unfading flower color ranging between Cherry and Rose Red.

No references cited.

ROBERT E. BAGWILL, Primary Examiner